United States Patent [19]

Riediker et al.

[11] Patent Number: 4,826,965
[45] Date of Patent: May 2, 1989

[54] METAL COMPLEXES CONTAINING OPTICALLY ACTIVE SUGAR LIGANDS, A PROCESS FOR THEIR PREPARATION AND THEIR USE AS CHIRAL REACTANTS FOR SYNTHESIS OF ALCOHOLS AND AMINES

[75] Inventors: Martin Riediker, Riehen; Robert W. Lang, Pratteln; Rudolf Duthaler, Bettingen; Peter Herold, Basel; Konrad Oertle, Therwil; Guido Bold, Frick, all of Switzerland

[73] Assignee: Ciba-Geigy Corporation, Ardsley, N.Y.

[21] Appl. No.: 76,250

[22] Filed: Jul. 21, 1987

[30] Foreign Application Priority Data

Jul. 23, 1986 [CH] Switzerland ............ 2941/86

[51] Int. Cl.$^4$ .............. C07F 7/28; C07H 23/00; C07H 15/04
[52] U.S. Cl. ............... 536/18.1; 536/121; 536/124; 536/127; 536/120
[58] Field of Search .............. 536/18.1, 121, 127

[56] References Cited

U.S. PATENT DOCUMENTS 4,176,228 11/1979 Hartung ............... 536/18.1
4,490,525 12/1984 Hayatsu et al. ........ 536/18.1

OTHER PUBLICATIONS

T. D. Inch et al., Tetrahedron Letters 41, 3657 (1969).
A. G. Olivero et al., Helv. Chim. Acta 64, 2485 (1981).
M. T. Reetz et al., Organometallics 3, 1716 (1984).
D. Seebach et al., Chem. Ber. 118, 3673 (1985).
Tetrahedron Letters, 41 pp. 3657–3660 (1969).
Helvetica Chimica Acta, 64 (1981) pp. 2485–2488.
Organomettalics 3, (1984) pp. 1716–1717.
D. Seebach, et al., Chem. Ber. 118, pp. 3673–3682 (1985).
Angew. Chem. International Edition, vol. 10, (1971) pp. 871–872.

Primary Examiner—A. Lionel Clingman
Attorney, Agent, or Firm—Harry Falber; Luther A. R. Hall

[57] ABSTRACT

Compounds of the forulae I and Ia

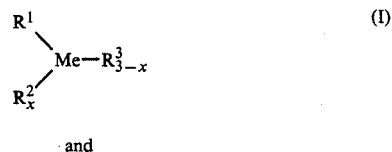

and

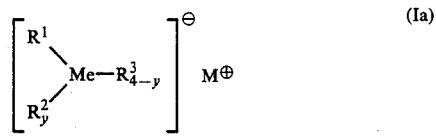

in which $R^1$ is a group which can be transferred to carbonyl or imine compounds, for example alkyl, allyl, vinyl or the radical of an enol or enamine, $R^2$ is, for example, cyclopentadienyl, $R^3$ is the radical of an optically active sugar or sugar derivative, Me is Ti, Zr or Hf, x is 0, 1 or 2 and y is 0, 1, 2 or 3, $M^\oplus$ is Li$\oplus$, Na$\oplus$, K$\oplus$, MgY$\oplus$, ZnY$\oplus$, CdY$\oplus$, HgY, CuY$\oplus$ or quaternary ammonium, Y being halogen, are suitable for use as chiral reactants for compounds containing aldehyde, keto and/or N-substituted imine groups.

15 Claims, No Drawings

METAL COMPLEXES CONTAINING OPTICALLY ACTIVE SUGAR LIGANDS, A PROCESS FOR THEIR PREPARATION AND THEIR USE AS CHIRAL REACTANTS FOR SYNTHESIS OF ALCOHOLS AND AMINES

The invention relates to titanium, zirconium or hafnium complexes containing optically active sugar ligands, a radical which can be transferred to carbonyl groups or carbonyl-analogous groups and, if appropriate, an achiral radical, to a process for their preparation and to their use as enantioselective reactants for aldehydes, ketones and N-substituted imines.

T. D. Inch et al. report in Tetrahedron Letters, No. 41, pages 3657–3660 (1969) that the reaction of prochiral ketones with chiral magnesium Grignard sugar complexes gives chiral secondary alcohols. The stereoselectivity of the reaction is relatively low. Thus the optical yields are in most cases about 25% and only in two cases are optical yields of 65 or 70% achieved.

It is known from Helvetica Chimica Acta, Vol. 64, Fasc. 7, No. 243, pages 2485–2488 (1981), Organometallics 3, pages 1716–1717 (1984) and Chem. Ber. 118, 3673–3682 (1985) that titanium compounds containing a transferable group and a radical derived from a chiral monohydroxy or dihydroxy compound can be reacted with aldehydes to give secondary alcohols. Aliphatic chiral hydroxy compounds as ligands result in only moderate stereoselectivity, whereas high optical yields can be achieved with chiral binaphthol as ligand. The chiral ligands used are difficult of acess and expensive.

A need exists for cheap chiral organotitanium reagents which have a high stereoselectivity when reacted with prochiral aldehydes, ketones and imines and in which the chiral ligands are derived from chiral hydroxy compounds which are readily accessible in industrial quantities, for example natural chiral hydroxy compounds.

The invention relates to compounds of the formulae I and Ia

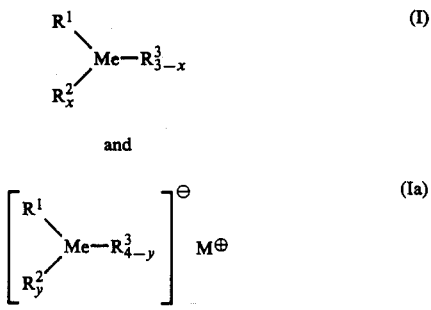

in which

Me is tetravalent titanium, zirconium or hafnium, $R^1$ is linear or branched alkyl, alkenyl, alkynyl, cycloalkyl or cycloalkenyl which is unsubstituted or substituted by $C_1$–$C_4$-alkyl, or is aryl, alkaryl, aralkyl, alkaralkyl, aralkenyl, alkaralkenyl, aralkynyl or alkaralkynyl which are unsubstituted or monosubstituted or polysubstituted by $(C_6H_5)_2P$—, $(R^5O)_2P(O)$—, $R_3^5Si$—, $R_3^5SiO$—, $R^5SO_2$—, —S—$C_2$–$C_4$-alkylene-S—, —O—$C_2$–$C_4$-alkylene-O—, $R^5$ being phenyl, benzyl or $C_1$–$C_8$-alkyl, or is cyano, F, nitro, $C_1$–$C_{12}$-alkylthio, $C_1$–$C_{12}$-alkoxy, secondary amino or —$COR^4$ in which $R^4$ is the radical of a monohydric alcohol; or $R^1$ is a radical of an enol, enamine or enehydrazine;

$R^2$ is cyclopentadienyl, alkoxy, cycloalkoxy, cycloalkylalkoxy, aryloxy, aralkyloxy, alkylthio, arylthio or aralkylthio which is unsubstituted or substituted by alkyl, alkenyl, alkoxy, cycloalkyl, aryl, aralkyl, trialkoxysilyl, trialkylsilyl or halogen; or $R^2$ is halogen, pseudohalogen, acyloxy, acylamino or trialkylsilyloxy, $R^3$ is the radical, diminished by a hydroxyl or thiol group or an amine hydrogen atom, of a protected, monohydroxy-functional, monothiol-functional or monoamine-functional, optically active sugar, thiosugar or amino-sugar or derivatives thereof belonging to the group of sugar alcohols; esters of a sugar acid, aldo-sugar acid or keto-sugar acid; amino-sugars, sugar mercaptals or deoxy-sugars, x is 0, 1 or 2 and y is 0, 1, 2 or 3 and $M^\oplus$ is $Li^\oplus$, $Na^\oplus$, $K^\oplus$, $MgY^\oplus$, $ZnY^\oplus$, $CdY^\oplus$, $HgY^\oplus$, $CuY^\oplus$ or quaternary ammonium, Y being halogen.

All the following preferences can be combined to give any desired groups composed of at least two preferred embodiments.

The compounds of the formula I are preferred. Protected and monohydroxy-functional, monothiol-functional or monoamino-functional means that the hydroxyl, thiol or amino groups of the sugar or sugar derivative are protected except for one OH, SH or NH group. Monohydroxy-functional sugars or sugar derivatives are preferred. Me is preferably Ti.

Optically active means containing predominantly one enantiomer, preferably an essentially pure enantiomer.

$R^1$ is a group which can be transferred to carbonyl and imine compounds. As alkyl, $R^1$ preferably contains 1 to 18 C atoms, especially 1–12 C atoms. Examples are methyl, ethyl, n-propyl, isopropyl, n-, i- or t-butyl, pentyl, hexyl, heptyl, octyl, nonyl, decyl, undecyl, dodecyl, tetradecyl, hexadecyl, octadecyl and eicosyl. Methyl, ethyl, propyl and butyl which can be substituted as indicated above are particularly preferred.

As alkenyl, $R^1$ preferably contains 2 to 12 C atoms, especially 2 to 6 C atoms. It can be either alkenylalkyl of the formula $(C_nH_{2n}\text{-}1\text{+}C_mH_{2m}\text{—}$ in which n is a number from 2 to 12, preferably 2 to 6, and m is a number from 1 to 6, preferably 1 or 2, or alkylvinyl which preferably has 1 to 10 C atoms in the alkyl group. Examples are: allyl, 1-methylallyl, 2-methylallyl, but-2-en-4-yl, but-1-en-3-yl, pent-3-en-5-yl, pent-1-en-3-yl, hex-4-en-6-yl hex-2en-4-yl, hept-2-en-1-yl, hept-3-en-5-yl, oct-6-en-8-yl, oct-2-en-4-yl, non-2-en-2-yl, dec-8-en-10-yl, dodec-3-en-12-yl, vinyl, crotonyl, n-but-1-en-1-yl, but-2-en-3-yl, pent-1-en-2-yl and hex-1-en-1-yl. $R^1$ is preferably vinyl or allyl. $R^1$ is particularly preferentially allyl.

As alkynyl, $R^1$ preferably contains 2–12 C atoms, especially 2–6 C atoms. The alkynyl group can be either in the carbon chain or can be terminal. Examples are: ethynyl, prop-2-yn-3-yl, prop-1-yn-3-yl, but-1-yn-4-yl, but-3-yn-4-yl, pent-4-yn-5-yl, pent-3-yn-5-yl, pent-2-yn-4-yl, pent-1-yn-5-yl and hex-1-yn-6-yl. Ethinyl and propargyl are preferred.

As cycloalkyl and cycloalkenyl, $R^1$ preferably contains 3–8, especially 3–6 and particularly 5 or 6 ring C atoms and can be substituted by $C_1$–$C_4$-alkyl. Examples are: cyclopropyl, cyclopropenyl, cyclobutyl, cyclobutenyl, cyclopentyl, cyclohexyl, cyclopent-1-en-3-yl, cyclopent-1-en-1-yl, cyclohex-1-en-3-yl, cyclohex-2-en-1-yl, cyclohept-1-en-3-yl or cyclooct-1-en-3-yl. As aryl, $R^1$ preferably contains 6–12 C atoms and is preferably naphthyl and especially phenyl. As alkaryl, $R^1$ preferably contains 7 to 16 C atoms. The aryl is preferably phenyl. Examples are: methylphenyl, dimethylphenyl, ethylphenyl, n-propylphenyl, isopropylphenyl, n-, i- and t-butylphenyl, di-t-butylphenyl, hexylphenyl, octylphenyl and decylphenyl.

As aralkyl, $R^1$ preferably contains 7 to 16 C atoms, especially 7–10 C atoms. The aryl is preferably phenyl. Examples are: benzyl, 1-phenylethyl, 2-phenylethyl, 1-phenylpropyl, 2-phenylpropyl, phenylbutyl, phenylpentyl and phenylhexyl. Benzyl and 1-phenylethyl or 2-phenylethyl are preferred.

As alkaralkyl, $R^1$ can preferably contain 8–16 C atoms. The aryl is preferably phenyl. Examples are: methylbenzyl, ethylbenzyl, n-propylbenzyl, isopropylbenzyl, dimethylbenzyl, n-, i- or t-butylbenzyl, di-t-butylbenzyl, hexylbenzyl, nonylbenzyl, 1-methylphenyleth-2-yl, 2-methyl-phenyleth-2-yl and 1-methylphenylprop-3-yl.

As aralkenyl, $R^1$ preferably contains 8 to 16 C atoms. The aryl is preferably phenyl. Examples are: phenylvinyl, 1-phenylprop-1-en-3-yl, 2-phenylprop-2-en-1-yl, 3-phenylprop-1-en-3-yl, phenylbutenyl, phenylpentenyl and phenylhexenyl.

As alkaralkenyl, $R^1$ preferably contains 9 to 16 C atoms. The aryl is preferably phenyl. Examples are: methylphenylvinyl, ethylphenylvinyl, dimethylphenylvinyl, 1-methylphenylprop-2-en-3-yl and 2-methylphenylprop-2-en-3-yl.

As aralkynyl, $R^1$ preferably contains 8 to 16 C atoms. The aryl is preferably phenyl. Examples are: phenylethynyl, phenylpropynyl and 1-phenylbut-3-yn-4-yl.

As alkaralkynyl, $R^1$ preferably contains 9 to 16 C atoms. The aryl is preferably phenyl. Examples are: methylphenylethynyl and methylphenylpropargyl.

Some examples of radicals $R^1$ are $—CH_2P(O)(OR^5)_2$, vinyl, allyl and substituted allyl radicals, for example $—CH_2CH=CH—P(C_6H_5)$, $—CH(SR^5)CH=CH—SiR_3^5$

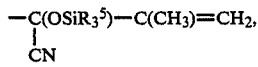

$—CH_2—CH=CH—SO_2—R^5$, $—CH_2—CH=CH—OR'$ and

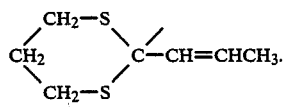

$R^5$ can be as defined above. $R'$ can be, for example, $C_1-C_8$-alkyl, methoxymethyl, methoxyisopropyl, 1-trimethylsilyleth-2-yl or $SiR_3^5$.

The enol radical $R^1$ is attached to the metal Me via the enol oxygen atom. The enols can be linear or cyclic. The enol radical $R^1$ preferably contains up to 20 C atoms, especially 2 to 16 C atoms. The cyclic enols can contain 3–8 ring atoms, especially 4–6 ring atoms, and the ring can be formed from atoms belonging to the group C, O, S and N. The enol radical $R^1$ can, for example, have the general formula

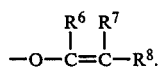

$R^6$ can be, for example, H, substituted or unsubstituted $C_1-C_8$-alkyl, $C_1-C_8$-alkoxy, $C_1-C_8$-alkylthio, cycloalkyl having 3–6 ring C atoms, phenyl, benzyl, phenoxy, phenylthio, benyzyloxy, benzylthio, secondary amino, $—OB(OC_1-C_8$-alkyl$)_2$, $—OSn(R^9)_3$ in which $R^9$ is $C_1-C_8$-alkyl, phenyl or benzyl, $—OTi—(R^9)_3$, $—OLi$ or $—OSi(R^5)_3$. $R^7$ and $R^8$ can independently be H, F or substituted or unsubstituted $C_1-C_8$-alkyl, $C_1-C_8$-alkoxy, $C_1-C_8$-alkylthio, cycloalkyl having 3 to 6 ring C atoms, phenyl, benzyl, phenoxy, phenylthio, benzyloxy, benzylthio, secondary amino or $—OSi(R^5)_3$. Possible substituents are those mentioned for $R^1$. The secondary amino group can contain $C_1-C_8$-alkyl, phenyl, benzyl or $(R_3^5)Si$ groups. It can also be a heterocyclic secondary amino group, preferably containing 4–6 ring atoms belonging to the group of C, O, S, Si and N. $R^6$ and $R^7$ or $R^7$ and $R^8$ together can, jointly with the C atoms to which they are attached, form a 3-membered to 8-membered, preferably 4-membered to 6-membered, carbocyclic or heterocyclic ring, and the heterocyclic ring can contain atoms belonging to the group of C, O, S and N. The rings can be substituted as defined above for $R^1$. Enols of glycine derivatives which have, for example, the formula

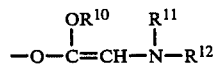

form a preferred group. $R^{10}$ can be, for example, benzyl, phenyl or $C_1-C_8$-alkyl. $R^{11}$ and $R^{12}$ can be $C_1-C_8$-alkyl, phenyl or benzyl or they can, together with the N atom, form a heterocyclic structure which can contain further hetero atoms belonging to the group of O, S or N. $R^{10}$ and $R^{11}$ together can also be methylene or ethylene. $R^{11}$ and $R^{12}$ can also be detachable protective groups, for example $R_3^5Si$-5 or $—SiR_2^5CH_2CH_2SiR_2^5—$. $R^{10}$, $R^{11}$ and $R^{12}$ can be substituted as defined above for $R^1$. Enol radicals of the formula

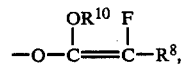

in which $R^8$ and $R^{10}$ are as defined above form another preferred group.

$R^1$ can also be the radical of an enamine or enehydrazine attached to the metal Me via an N atom. These can be linear or cyclic enamines or enehydrazines, preferably containing up to 20 C atoms, especially 2–16 C atoms. The cyclic enamines and enehydrazines can contain 3–8 ring atoms, especially 4–6 ring atoms, and the ring can be formed from atoms belonging to the group of C, O, S and N. The N atom of the enamine group can be substituted, preferably by $C_1-C_8$-alkyl, phenyl, benzyl or protective groups, for example $R_3^5Si—$.

The enamine radical or enehydrazine radical can, for example, have the formula

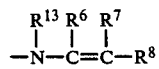

in which $R^6$, $R^7$ and $R^8$ are as defined above for the enol radical $R^1$, $R^6$ and $R^{13}$, together with the C—N group, or $R^7$ and $R^{13}$, together with the —N—C=C— group, form a 3-membered to 8-membered, preferably 4-membered to 6-membered heterocyclic structure which can contain further hetero atoms belonging to the group of O, S and N, and $R^{13}$ is H, $C_1-C_8$-alkyl, phenyl, benzyl, $C_1-C_8$-alkoxy, phenoxy, benzyloxy, $R_3{}^5Si$— or —$NR^{14}R^{15}$ in which R is as defined above and $R^{14}$ and $R^{15}$ are H, $C_1-C_8$-alkyl, phenyl or benzyl. In a preferred group, $R^6$ is H, $C_1-C_8$-alkyl, phenyl or benzyl and $R^7$ and $R^8$ are H. The enol, enamine and enehydrazine radicals are C-nucleophilic radicals, capable of undergoing aldol reactions.

As the radical of an enol, $R^1$ can also be a ketone, ester or amide enolate, and contains especially up to 16 C atoms, in particular 4–16 C atoms. The enolates can be derived from $\beta$-ketoaldehydes, 1,3-diketones, $\beta$-ketocarboxylic acid esters and $\beta$-ketocarboxamides. The ester group preferably contains radicals of aliphatic $C_1-C_6$-alcohols. The N atom in the amide group can be monosubstituted or disubstituted, preferably with $C_1-C_6$-alkyl. Examples are: $\beta$-ketobutyraldehyde, acetylacetone, benzoylacetone, ethylacetoacetate and acetoacetamide.

The radical $R^1$ can be monosubstituted or polysubstituted, preferably monosubstituted to trisubstituted and particularly monosubstituted or disubstituted. If the substituent is alkoxy or alkylthio, it preferably contains 1–6 C atoms. $R^4$ is preferably the radical of an aliphatic alcohol having 1 to 6 C atoms. Possible examples are radicals of aliphatic or cycloaliphatic alcohols. Examples are: methoxy, ethoxy, n-propoxy, isopropoxy, n-, i- and t-butoxy, pentoxy, hexyloxy, cyclopentyloxy and cyclohexyloxy.

As alkyl, $R^5$ preferably contains 1–6 C atoms, especially 1–4 C atoms. The alkoxy, alkylthio, —S—$C_2-C_4$-alkylene-S— and —O—$C_2-C_4$-alkylene-O— can be attached to a C atom; these are then acetal or ketal groups.

The secondary amino, in the sense of a substituent, can have the formula —$NR^{16}R^{17}$ in which $R^{16}$ and $R^{17}$ are $C_1-C_{12}$-alkyl, preferably $C_1-C_6$-alkyl, cyclopentyl, cyclohexyl, phenyl, benzyl or $R_3{}^5Si$—, or $R^{16}$ and $R^{17}$ together are $C_3-C_6$-alkylene, 3-oxapentylene or —$SiR_2{}^5$—$C_2-C_3$-alkylene-$SiR_2{}^5$— and $R^5$ is as defined above.

In a preferred subgroup $R^1$ is linear or branched $C_1-C_{18}$-alkyl, $C_2-C_{12}$-alkenyl, $C_2-C_{12}$-alkynyl, cycloalkyl having 3–8 ring C atoms, cycloalkenyl having 3 to 8 ring C atoms, $C_6-C_{12}$-aryl, $C_7-C_{16}$-alkaryl or aralkyl, $C_8-C_{16}$-alkaralkyl, $C_8-C_{16}$-aralkenyl, $C_9-C_{16}$-alkaralkenyl, $C_8-C_{16}$aralkynyl or $C_9-C_{16}$-alkaralkynyl which is unsubstituted or monosubstituted or polysubstituted by secondary amino, cyano, nitro, $C_1-C_6$-alkylthio, $C_1-C_6$-alkoxy or —$COR^4$ in which $R^4$ is $C_1-C_{12}$-alkoxy; or $R^1$ is the radical of an enol, enamine or enehydrazine which is attached via the enol oxygen atom or via the enamine nitrogen atom.

In a further preferred subgroup, $R^1$ is linear or branched $C_1-C_6$-alkyl, $C_2-C_6$-alkenyl, $C_2-C_6$-alkynyl, cycloalkyl having 3–6 ring C atoms, cycloalkenyl having 3 to 6 ring C atoms, phenyl, ($C_1-C_{10}$-alkyl)-phenyl, phenyl-($C_1-C_2$-alkyl), ($C_1-C_8$-alkyl)-phenyl-($C_1-C_2$-alkyl), phenylvinyl, phenylethynyl, phenylpropargyl, ($C_1-C_8$-alkyl)-phenylvinyl, ($C_1-C_8$-alkyl)-phenylethynyl or ($C_1-C_7$-alkyl)-phenylpropargyl which is unsubstituted or monosubstituted or polysubstituted by secondary amino, cyano, nitro, $C_1-C_6$-alkoxy, $C_1-C_6$-alkylthio or -$COR^4$ in which $R^4$ is $C_1-C_{12}$-alkoxy; or $R^1$ is the radical of an enol, enamine or enehydrazine having up to 20 C atoms which is attached via an enol oxygen atom or enamine nitrogen atom.

$R^1$ is particularly preferably linear or branched $C_1-C_4$-alkyl, vinyl, allyl, ethynyl, propargyl, cyclopentyl, cyclohexyl, cyclopentenyl, cyclohexenyl, phenyl, methylphenyl, benzyl, 1-phenyleth-2-yl, methylbenzyl, phenylvinyl, methylphenylvinyl, phenylethynyl, phenylpropargyl, methylphenylethynyl, dimethylphenylethynyl or dimethylphenylpropargyl which is unsubstituted or monosubstituted or polysubstituted by secondary amino, cyano, nitro, $C_1-C_6$-alkoxy, $C_1-C_6$-alkylthio or —$COR^4$ in which $R^4$ is $C_1-C_{12}$-alkoxy; or $R^1$ is the radical of an enol, enamine or enehydrazine having 2–16 C atoms which is attached via the enol oxygen atom or via the enamine nitrogen atom.

As cyclopentadienyl, alkoxy, cycloalkoxy, cycloalkylalkoxy, aryloxy, aralkyloxy, alkylthio, arylthio and aralkylthio, $R^2$ can be substituted, for example by 1 to 3, preferably 1 or 2, substituents. Examples of suitable substituents are alkyl which preferably has 1 to 6 C atoms, alkenyl which preferably has 2 to 6 C atoms, alkoxy which preferably has 1 to 6 C atoms, cycloalkyl which preferably has 5 or 6 ring C atoms, aryl which preferably has 6 to 12 C atoms, aralkyl which preferably has 7 to 13 C atoms, trialkoxysilyl which preferably has 1 to 6 C atoms in the alkoxy groups, trialkylsilyl which preferably has 1 to 6 C atoms in the alkyl groups, or halogen, preferably F, Cl and Br. Aryl is especially phenyl, and aralkyl is especially benzyl.

As alkoxy, $R^2$ preferably contains 1 to 18 C atoms, especially 1 to 12 C atoms. Examples are: methoxy, ethoxy, n-propoxy, isopropoxy, n-, i- or t-butoxy, pentoxy, hexoxy, 2-ethylhexoxy, octyloxy, nonyloxy, decyloxy, undecyloxy, dodecyloxy, tri-t-butylmethoxy, tetradecyloxy or octadecyloxy. As cycloalkoxy and cycloalkylalkoxy, $R^2$ preferably contains 4–8 ring C atoms, especially 5 or 6 ring C atoms, and, in total, preferably 4–18 C atoms, especially 4–12 C atoms. Examples are cyclopentoxy, cyclohexoxy, cyclohexylmethoxy and triptycen-9-oxy.

As aryloxy, $R^2$ is especially $C_6-C_{12}$-aryloxy, preferably naphthoxy or phenoxy; as aralkoxy, it is especially $C_7-C_{12}$-aralkoxy, preferably benzyloxy or phenylethoxy.

As alkylthio, $R^2$ preferably contains 1–18 C atoms, especially 1–12 C atoms. The alkylthio can be linear or branced. Examples are: methylthio, ethylthio, n-propylthio, isopropylthio, n-, i- or t-butylthio, pentylthio, hexylthio, octylthio, dodecylthio and octadecylthio.

As arylthio, $R^2$ especially contains 6–12 C atoms and is preferably phenylthio or naphthylthio; as aralkylthio, $R^2$ especially has 7–16 C atoms and is preferably benzylthio or phenylethylthio.

As halogen, $R^2$ can be F, Cl, Br or I, and as pseudohalogen can be CN, CNS or CNO.

As acyloxy and acylamino, $R^2$ preferably contains 1 to 18 C atoms, especially 1 to 12 C atoms. The N atom in the acylamino can be substituted by $C_1-C_6$-alkyl. The acyloxy and acylamino can be derived, for example, from aliphatic $C_1-C_{18}$-carboxylic acids, preferably $C_1-C_{12}$-carboxylic acids, aromatic $C_7-C_{13}$-carboxylic acids or araliphatic $C_8-C_{14}$-carboxylic acids. The following are examples of acids from which acyloxy and acylamino can be derived: formic acid, acetic acid, chloroacetic acid, trichloroacetic acid, trifluoroacetic acid, propionic acid, butyric acid, benzoic acid, chlorobenzoic acid and phenylacetic acid.

As trialkylsilyloxy, $R^2$ preferably contains 1 to 6 C atoms in the alkyl groups. Examples of alkyl groups are: methyl, ethyl, n-propyl, isopropyl, n-, i- or t-butyl, pentyl and hexyl. Examples of trialkylsilyloxy are: trimethylsilyloxy, triethylsilyloxy, triisopropylsilyloxy, tri-nbutylsilyloxy and tri-t-butylsilyloxy.

In a preferred embodiment, $R^2$ is cyclopentadienyl, $C_1$-$C_{18}$-alkoxy, $C_6$-$C_{12}$-aryloxy, $C_7$-$C_{16}$-aralkoxy, $C_1$-$C_{18}$-alkylthio, $C_6$-$C_{12}$-arylthio or $C_7$-$C_{16}$-aralkylthio which is unsubstituted or substituted by $C_1$-$C_6$-alkyl, $C_2$-$C_6$-alkenyl, $C_1$-$C_6$-alkoxy, cycloalkyl having 5 or 6 ring C atoms, phenyl, benzyl, trialkoxysilyl having 1 to 6 C atoms in the alkoxy groups, trialkylsilyl having 1 to 6 C atoms in the alkyl Y groups, F, Cl or Br; or $R^2$ is halogen, pseudohalogen, $C_1$-$C_{18}$-acyloxy, $C_1$-$C_{18}$-acylamino or trialkylsilyloxy having 1 to 6 C atoms in the alkyl groups.

In another preferred embodiment, $R^2$ is cyclopentadienyl, $C_1$-$C_6$-alkoxy, phenoxy, benzyloxy, $C_1$-$C_6$-alkylthio, phenylthio or benzylthio which is unsubstituted or substituted by $C_1$-$C_6$-alkyl, $C_2$-$C_6$-alkenyl, $C_1$-$C_6$-alkoxy, cycloalkyl having 5 or 6 ring C atoms, phenyl, benzyl, trialkoxysilyl having 1 to 6 C atoms in the alkoxy groups, trialkylsilyl having 1 to 6 C atoms in the alkyl groups, F, Cl or Br; or $R^2$ is Cl, Br, I, CN, CNS, CNO, $C_1$-$C_{12}$-acyloxy, $C_1$-$C_{12}$-acylamino or trialkylsilyloxy having 1 to 4 C atoms in the alkyl groups.

$R^2$ is particularly preferably cyclopentadienyl or methylcyclopentadienyl.

$R^3$ is preferably the radical of a protected monohydroxy-functional, monothiol-functional or monoamino-functional $C_3$-$C_7$-monosaccharide or corresponding disaccharides or trisaccharides, or derivatives thereof belonging to the group of the sugar alcohols, esters of a sugar acid, aldosugar acid or keto-sugar acid, amino-sugars, deoxysugars or sugar-mercaptals. $R^3$ is particularly preferably the radical of a $C_3$-$C_7$-monosaccharide, especially a $C_5$ or $C_6$ monosaccharide, or derivatives thereof. In particular, $R^3$ is the radical of a protected furanose or pyranose.

The hydroxyl groups of the sugars and their derivatives are protected. Possible suitable protective groups are $C_1$-$C_8$-acyl, $C_1$-$C_8$-alkyl, benzyl, diphenylmethyl, trityl, $C_1$-$C_8$-alkylidene, $C_3$-$C_8$-cycloalkylidene, triphenylsilyl or trialkylsilyl having 1 to 8 C atoms in the alkyl groups, and also diphenyl-Si= or ($C_1$-$C_8$-alkyl)$_2$-Si= and diphenylSN= or ($C_1$-$C_8$-alkyl)$_2$Sn=. The alkylidene can be substituted, for example by phenyl. The acyl preferably contains 2 to 7 C atoms, the alkyl preferably 1 to 4 C atoms, the alkyl groups in the trialkylsilyl preferably 1 to 6 C atoms, the alkylidene preferably 2 to 6 C atoms and the cycloalkylidene preferably 5 or 6 ring C atoms. Examples are: methyl, ethyl, n-propyl, isopropyl, n-, i- or t-butyl, formyl, acetyl, propionyl, pivaloyl, benzoyl, methy-lidene, ethylidene, 1,1-propylidene, 2,2-propylidene, 1,1-butylidene, 2,2-butylidene, benzylidene, pentylidene, hexylidene, cyclohexylidene, trimethylsilyl, dimethyl-t-butylsilyl, (1,1,2,2-tetramethylethyl)-dimethylsilyl, (t-butyl)$_2$Si=, (CH$_3$)$_2$Si=, (isopropyl)$_2$Si= and (n-butyl)$_2$Sn=. Further suitable protective groups are $C_1$-$C_8$-alkoxy-B or phenoxy-B or phenyl-B and also alkoxymethyl, for example methoxymethyl, ethoxymethyl or (trimethylsilylethoxy)methyl.

The sugars from which $R^3$ is derived can be, for example, aldoses or ketoses. Examples are: glyceraldehyde, erythrose, threose, arabinose, ribose, xylose, lyxose, glucose, mannose, allose, galactose, fructose, gulose, altrose, idose, talose, ribulose, erythrulose, xylulose, psicose, sorbose and tagatose. The sugars can be in an open-chain or cyclized form, for example in the form of furanoses or pyranoses.

Examples of disaccharides and trisaccharides are sucrose, maltose, lactose and raffinose.

Examples of sugar alcohols from which $R^3$ can be derived are sorbitol and mannitol.

The sugar acids, aldo- and keto-sugar acids from which $R^3$ can be derived can be in the form of lactones or esters, the ester group or ester groups preferably containing $C_1$-$C_4$-alkyl, in particular methyl. Examples of such acids are gluconic acid, saccharic acid, mannosaccharic acid, mannonic acid and uronic acids, for example glucuronic acid, and also neuraminic acid and ascorbic acid.

Glucosamine, galactosamine and mannosamine may be mentioned as examples of amino-sugars from which $R^3$ can be derived.

Glucose dimethyl mercaptal and thioglucoside may be mentioned as examples of sugar mercaptals from which $R^3$ can be derived.

2-Deoxyribofuranose, rhamnose, fucose and digitoxose are examples of deoxy-sugars from which $R^3$ can be derived.

The sugars and sugar derivatives from which $R^3$ is derived are in the form of virtually pure enantiomers.

1,2:5,6, -Di-O-isopropylidene-α-D-glucofuranose is a preferred example of a protected, monohydroxy-functional sugar from which the radical $R^3$ can be derived.

In formula I x is preferably 1, and in formula Ia y is preferably 2, especially 1

In the group $M^\oplus$ of the formula Ia Y is preferably Cl, Br or I. $M^\oplus$ is preferably $Li^\oplus$, $MgCl^\oplus$, $MgBr^\oplus$, $ZnCl^\oplus$, $ZnBr^\oplus$, $CdCl^\oplus$, $CdBr^\oplus$ or tetralkylammonium having 1 to 6 C atoms in the alkyl groups. $M^\oplus$ is particularly preferably $MgY^\oplus$ in which Y is Cl, Br or I.

The compounds of the formulae I and Ia can be prepared, for example, by reacting a compound of the formula II $$R_x^2 R_{3-x}^3 MeX \qquad (II)$$

or a compound of the formula IIa $$R_y^2 R_{4-y}^3 Me \qquad (IIa)$$

in the presence of an inert solvent and an inert protective gas with a compound of the formula III $$R^1 \ominus M^\oplus \qquad (III)$$

in which Me, $R^1$, $R^2$, $R^3$, $M^\oplus$, x and y are as defined above and X is an anion. Examples of suitable anions are $PF_6^\ominus$, $SbF_6^\ominus$, $BF_4^\ominus$, $CF_3COO^\ominus$, sulfonate (for example tosylate) and, particularly, $Cl^\ominus$ or $Br^\ominus$.

The invention also relates to the compounds of the formula II and IIa, which can be obtained in a simple manner by reacting 1 mole of a salt of the formulae $$R_x^2 MeX_{4-x} \text{ or } R_y^2 MeX_{4-y}$$

with 1 to 3 or 1 to 4 moles, respectively, of an optically active, protected, monohydroxy-functional, monothiol-functional or monoamino-functional sugar, thio-sugar, amino-sugar or derivatives thereof belonging to the group of sugar alcohols; esters of a sugar acid, aldo sugar acid or keto sugar acid; amino-sugars, sugar mercaptals or deoxy-sugars of the formula $R^3H$. The reaction can be carried out at temperatures from −78° to +100° C., preferably in an inert solvent, for example ethers (diethyl ether, tetrahydrofuran, dioxane or ethylene glycol dimethyl ether). It is advantageous to carry out the reaction under an atmosphere of a protective gas, for example argon, and in the presence of a basic compound, in order to bind the HX which is formed. Examples of suitable basic compounds are alkali metal carbonates, such as sodium carbonate and sodium bicarbonate, and also amines, especially tertiary amines, for example triethylamine. The compounds are isolated by filtering off the precipitated halide and removing the solvent. The crude products thus obtained can be used further without purification. The titanium halides are known or can be prepared by known processes. Instead of the Me halides, it is also possible to employ compounds of the formula $R_4{}^4Me$ in which $R^4$ is especially alkyl. It is also possible to use compounds of the formula $R_2{}^1TiZ_4$-z in which Z is Cl or Br and z is 1, 2 or 3. If 3 mole of sugar are employed in this reaction, compounds, according to the invention, of the formula I of the type $R^1MeR_3{}^3$ are obtained directly.

The preparation of the compounds of the formula I and Ia is advantageously carried out at temperatures from −78° to +30° C. and in an inert solvent. Suitable solvents are, in particular, ethers. The reaction is carried out under a protective gas, for example argon. Precipitated $M^{\oplus}X^{\ominus}$ is filtered off. The crude product obtained after removing the solvent can be immediately used for further purposes.

The compounds according to the invention are excellently suitable for use as enantioselective reactants for compounds containing carbonyl and/or N-substituted imine groups. If $R^2$ is a cyclopentadienyl radical, the compounds are particularly suitable for the transfer of allyl, enol, enamine and enehydrazine groups. If $R^2$ is not a cyclopentadienyl radical, the compounds are suitable for the transfer of any $R^1$ group. The invention also relates to this use. The carbonyl compounds are preferably prochiral aldehydes and ketones; the reaction products, obtained in high yields, are chiral, secondary or tertiary alcohols or secondary amines or amino acids containing a large excess of one enantiomer. The synthesis of chiral active ingredients in the field of pharmaceuticals and agricultural chemicals has acquired considerable importance. The compounds according to the invention are suitable for the preparation of appropriate intermediates for the synthesis of such active ingredients or for the introduction of groups containing chiral C atoms in the final stage of the synthesis of such active ingredients. Thus it is possible, for example, to prepare in high yields pheromones for the control of insects. (−)-S-ipsenol, the synthesis of which is described in the examples, may be mentioned as an example.

In addition, the compounds according to the invention can be prepared cheaply from cheap starting materials. As derivatives of natural compounds they can be disposed of in an environmentally non-harmful manner by biological methods of degradation, especially as titanium and titanium oxide are known to be physiologically harmless. A large variety of sugars and sugar derivatives are known, so that it is also possible to provide reactants having a high effectiveness for specific carbonyl groups or N-substituted imine groups. The substituents in the imine can be the radicals mentioned above, such as alkyl, alkenyl, cycloalkyl, aryl and aralkyl. If these radicals are substituted by carboxyl or carboxyl ester groups, the reaction products obtained are amino acids or esters thereof.

The present invention also relates to a process for the preparation of secondary and tertiary alcohols and secondary amines, which comprises reacting aldehydes, ketones or N-substituted aldimines or ketimines with 1 mole of a compound of the formula I or Ia per mole of aldehyde, keto or imine group.

The reaction is advantageously carried out at temperatures from −80° to 30° C. in the presence of an inert solvent and under a protective gas. The reaction product is advantageously isolated by hydrolysis, extracting the product and purifying it in a customary manner. Examples of suitable inert solvents are ethers or hydrocarbons, such as pentane, hexane, cyclohexane, methylcyclohexane, benzene, toluene, xylene, diethyl ether, tetrahydrofuran or dioxane, nitriles, for example acetonitrile, or chlorinated hydrocarbons, for example methylene chloride, chloroform or chlorobenzene.

The following examples illustrate the invention. Cp is cyclopentadienyl and HODAG is the sugar according to Example 1a (abbreviation of diacetoneglucose). The determination of the excess of one enantiomer is effected by the following methods:

A. Polarimetry
   Reference:
   (S)-1-phenyl-3-buten-1-ol $(\alpha)_D=48.7°$ (c 6.92, benzene)
   A. F. Lee, Holding and W. A. Ross, J. Chem. Arc. 1954, 145.
B. GC analysis (DB-wax 30 m) of the MTP A-esters
   Reference:
   James A. Date, David L. Dull and Harry S. Mosher, JOC 34, 2543 (1969).
C. GC analysis (chirasil-L-val 50 M) of the derivatives with isopropyl isocyanate.
   Reference:
   W. König et al., Journal of Chromatography, 239 (1982) 227-231.
D. $^1$H-NMR shift method using optically active 1-(9'-anthryl)-2,2,2-trifluoroethanol.
E. As B, but with chirasil-L-val, 50 m.
F. HPLC analysis (column with cellulose triacetate).
G. As C, but without formation of derivatives.
H. HPLC analysis (R-ion DNBPG).
I. Derivatives with trifluoroacetic anhydride, then as C.

EXAMPLE 1

(a) Cyclopentadienylchlorotitanium bis-(1,2:5,6-di-O-isopropylidene-α-glucofuranose) complex A solution of 2.03 g (20.1 mmol) of triethylamine in 25 ml of absolute diethyl ether is added dropwise, in the course of 30 minutes and at room temperature (RT), to a solution of 2.15 g (9.8 mmol) of cyclopentadienyltitanium trichloride and 5.10 g (19.6 mmol) of 1,2:5,6-di-O-isopropylidene-α-glucofuranose in 60 ml of diethyl ether (distilled over sodium and benzophenone). The pale yellow suspension is stirred for a further 2 hours at RT, the triethylaminehydrochloride formed is filtered off with suction, under argon, and the solvent is distilled off in vacuo. The resulting oily, slightly yellowish crude product can immediately be used for further purposes. $^1$H-NMR spectrum (CDCl$_3$, 60 MHz): 1.31–1.49 (m, 24 H), 3.73–4.60 (m, 10 H), 5.07 (d, 2 Hz, 2 H), 5.83 (d, 4 Hz, 2 H), 6.62 (s, 5 H).

(b) Cyclopentadienylallyltitanium bis-(1,2:5,6-di-O-isopropylidene-α-glucofuranose) complex 9.8 mmol of cyclopentadienylchlorotitanium bis-(1,2:5,6-di-O-isopropylidene-α-glucofuranose) complex are dissolved in 100 ml of diethyl ether and cooled to 0° C., and 3.8 ml (9.8 mmol) of allylmagnesium chloride (2.6 molar solution in tetrahydrofuran) are added. The orange-red suspension is stirred for 1 hour at 0° C., filtered under argon and evaporated in vacuo. The air-sensitive oily crude product is immediately used for further purposes. $^1$H-NMR spectrum (CDCl$_3$, 60 MHz): 1.32–1.49 (m, 24 H), 3.23–4.53 (m, 15 H), 4.85 (d, 2 Hz, 2 H), 5.83 (d, 4 Hz, 2 H), 6.27 (s, 5 H).

EXAMPLE 2

(a) Cyclopentadienyltitanium tris-(1,2:5,6-di-O-isopropylidene-α-glucofuranose) complex A solution of 3.03 g (30 mmol) of triethylamine in 30 ml of diethyl ether is added dropwise, in the course of 30 minutes and at RT, to a solution of 2.19 g (10 mmol) of cyclopentadienyltitanium trichloride and 7.80 g (30 mmol) of 1,2:5,6-di-O-isopropylidene-α-glucofuranose in 60 ml of diethyl ether. The slightly yellow suspension is stirred for a further 2 hours at RT, the triethylamine hydrochloride formed is filtered off with suction, under argon, and the solvent is distilled off in vacuo. The resulting slightly yellowish crude product solidifies at room temperature and can immediately be used for further purposes. $^1$H-NMR spectrum (CDCl$_3$, 60 MHz): 1.28–1.47 (m, 36 H), 3.80–4.50 (m, 15 H), 4.83 (d, 2 Hz, 3 H), 573 (d, 4 Hz, 3 H), 6.48 (s, 5 H).

(b) Cyclopentadienyltitanium tris-(1,2:5,6-di-O-isopropylidene-α-glucofuranose) allylmagnesium chloride complex 10 mmol of cyclopentadienyltitanium tris-(1,2:5,6-di-O-isopropylidene-α-glucofuranose) complex are dissolved in 100 ml of diethyl ether and cooled to 0° C., and 3.85 ml (10 mmol) of allylmagnesium chloride (2.6 molar solution in tetrahydrofuran) are added. The orange-red solution is stirred for a further hour at 0° C. and is then immediately used for further purposes. $^1$H-NMR spectrum (CDCl$_3$, 60 MHz): 1.30–1.48 (m, 36 H), 3.50–4.57 (m, 20 H), 4.86 (d, 2 Hz, 3 H), 5.76 (d, 4 Hz, 3 H), 6.50 (s, 5 H).

Use Examples

EXAMPLE 3

Preparation of (R)-1-phenyl-3-buten-1-ol

A solution in 100 ml of diethyl ether of 9.8 mmol of cyclopentadienylallyltitanium bis-(1,2:5,6-di-O-isopropylidene-α-glucofuranose) complex according to Example 1 is cooled to −74° C. by means of a CO$_2$/acetone bath, and 0.89 ml (8.8 mmol) of freshly distilled benzaldehyde is added. The clear yellow solution is stirred for a further 2 hours at −74° C., and 50 ml of NH$_4$F solution (45% in water) are added. The beige emulsion is warmed to RT and separated in a separating funnel. The ether phase is extracted once with 50 ml and then with twice 30 ml of 2N HCl and is diluted with 300 ml of ether and is then washed with twice 300 ml of water and once with 300 ml of saturated NaCl solution, dried by means of MgSO$_4$, filtered and evaporated to dryness on a rotary evaporator. The crude product is flash chromatographed (45 g of silica gel, 25 cm length, diameter 2 cm, 10 ml/fraction, 0.3 bar, 1:5 ether/n-hexane) and distilled (boiling point 150° C./14 mbar); 1.02 g (79% yield) of a clear, colourless oil are obtained: $[\alpha]_D = +44.1°$ (c 6.5, benzene), 91% ee (methods A and B).

EXAMPLES 4–27

The reactions listed in the table below are carried out analogously to Example 3: S=solvent and T=reaction temperature.

TABLE

| Ex. | Carbonyl compound | Titanium complexes | Reaction conditions S | T[°C] | Product | Yield [%] | $[\alpha]_D$ | % ee | Method |
|---|---|---|---|---|---|---|---|---|---|
| 4 | 8.8 mmol Benzaldehyde | 9.8 mmol according to Ex. 1 | Toluene | −74° | 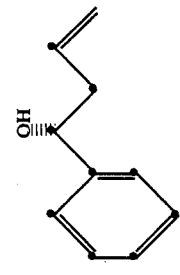 | 80 | +43.62 (c 6.52; Benzene) | 90 | A B C |
| 5 | 9 mmol Benzaldehyde | 10 mmol according to Ex. 2 | Diethyl ether | −74° | 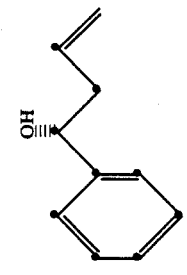 | 70 | +35.6 (c 6.7; Benzene) | 73 71 | A C |
| 6 | 7.8 mmol Cyclohexylaldehyde | 9.8 mmol according to Ex. 1 | Diethyl ether | −74° | 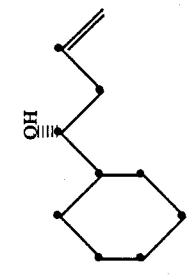 | 78 | +8.2 (c 0.55; Ethanol) | 92 | B |
| 7 | 7 mmol 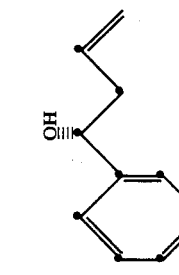 | 8 mmol according to Ex. 1 | Diethyl ether | 0° | | 98 | (+)[b] | 81 | C D |
| 8 | 7 mmol  | 8 mmol according to Ex. 1 | Tetrahydrofuran | −74° | | 85 | (+)[b] | 89 | C |

TABLE -continued

| Ex. | Carbonyl compound | Titanium complexes | Reaction conditions S | Reaction conditions T[°C.] | Product | Yield [%] | $[\alpha]_D$ | % ee | Method |
|---|---|---|---|---|---|---|---|---|---|
| 9 | 10 mmol, CH₃CH₂CH₂CH₂CHO | 12 mmol according to Ex. 1 | Diethyl ether | −74° | CH₃CH₂CH₂CH₂CH(OH)CH₂CH=CH₂ | 50 | (−)[b] | 94 | E |
| 10 | 10 mmol, CH₃CH₂CHO | 12 mmol according to Ex. 1 | Diethyl ether | −74° | CH₃CH₂CH(OH)CH₂CH=CH₂ | 67 | −8.5 (1.9, Benzene) | 94 | C |
| 11 | 36 mmol, 9-anthraldehyde | 44 mmol according to Ex. 1 | Diethyl ether | −74° | 9-anthryl-CH(OH)CH₂CH=CH₂ | 90 | +19.9 (5.93, Benzene) | 94 | F |
| 12 | 10 mmol, (CH₃)₃CCHO | 12 mmol according to Ex. 1 | Diethyl ether | −74° | (CH₃)₃CCH(OH)CH₂CH=CH₂ | 35 | +10.86 (10.53 Benzene) | 92 | C |
| 13 | 10 mmol, (CH₃)₂CHCHO | 12 mmol according to Ex. 1 | Diethyl ether | −74° | (CH₃)₂CHCH(OH)CH₂CH=CH₂ | 98 | (+)[b] | 92 | C |
| 14 | 10 mmol, CH₃(CH₂)₈CHO | 12 mmol according to Ex. 1 | Diethyl ether | −74° | CH₃(CH₂)₈CH(OH)CH₂CH=CH₂ | 88 | +10.38 (6.65, Benzene) | 92 | C |

TABLE -continued

| Ex. | Carbonyl compound | Titanium complexes | Reaction conditions S | T[°C] | Product | Yield [%] | $[\alpha]_D$ | % ee | Method |
|---|---|---|---|---|---|---|---|---|---|
| 15 | 10 mmol 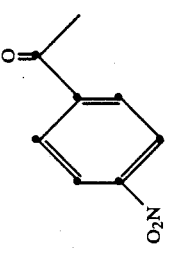 | 12 mmol according to Ex. 1 | Diethyl ether | −74° | 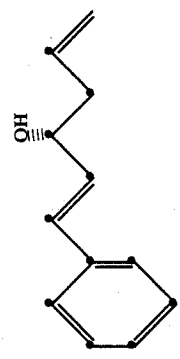 | 82 | +23.7 (5.1, Benzene) | 92 | C |
| 16 | 10 mmol  | 12 mmol according to Ex. 1 | Diethyl ether | −74° | 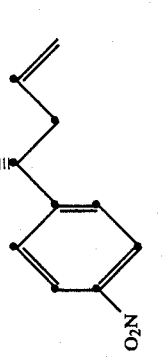 | 52 | +13.5 (9.73, Et₂O) | 90 | A C |
| 17 | 10 mmol 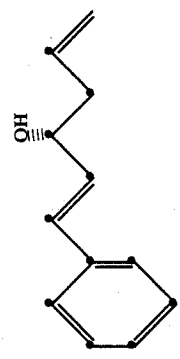 | 12 mmol according to Ex. 1 | Diethyl ether | −74° |  | 84 | +77.2 (10.24 Benzene) | 88 | C |
| 18 | 10 mmol 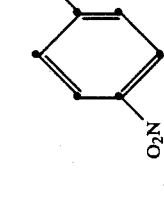 | 12 mmol according to Ex. 1 | Diethyl ether | −74° | | 61 | (−)[b] | 87 | E |
| 19 | 15 mmol 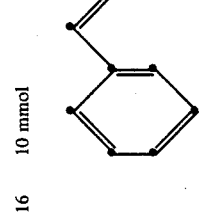 | 17.2 mmol according to Ex. 1 | Diethyl ether | −74° | | 55 | (−)[b] | 86 | C |

TABLE -continued
| Ex. | Carbonyl compound | Titanium complexes | Reaction conditions S | T[°C.] | Product | Yield [%] | [α]D | % ee | Method |
|---|---|---|---|---|---|---|---|---|---|
| 20 | 8.8 mmol 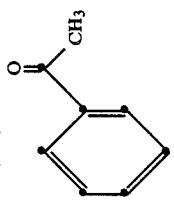 | 9.8 mmol according to Ex. 1 | Diethyl ether | 0° | 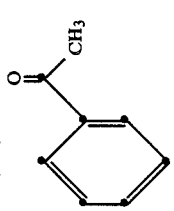 | 57 | +22.7 (5.78, Benzene) | 76 | A D |
| 21 | 8.8 mmol 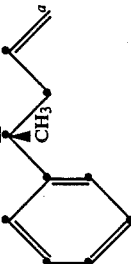 | 9.8 mmol according to Ex. 1 | Diethyl ether | 0° | 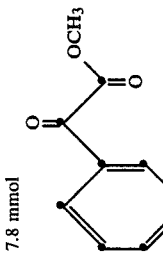 | 60 | −35.3 (6.92, CH$_2$Cl$_2$) | 52 | A D |
| 22 | 7.8 mmol 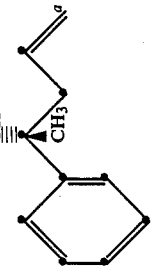 | 9.8 mmol according to Ex. 1 | Diethyl ether | 20° | 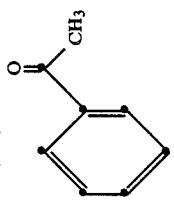 | 60 | +10.69 (5.55, Benzene) | 52 | D |
| 23 | 8.8 mmol 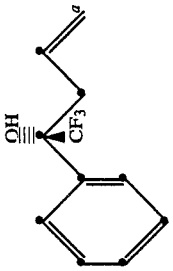 | 9.8 mmol according to Ex. 1 | Diethyl ether | 0° | 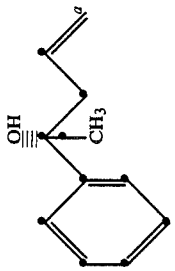 | 70 | (+)[b] | 44 | D |

TABLE -continued

| Ex. | Carbonyl compound | Titanium complexes | Reaction conditions S | Reaction conditions T[°C.] | Product | Yield [%] | [α]$_D$ | % ee | Method |
|---|---|---|---|---|---|---|---|---|---|
| 24 | 8 mmol (p-methoxyphenyl-N=CH-CO$_2$Et) | 10 mmol according to Ex. 1 | Diethyl ether | −20° | EtO$_2$C-CH(NH-p-methoxyphenyl)-CH$_2$CH=CH$_2$ [a] | 16 | b | 37 | G |
| 25 | 5 mmol (TosN=CH-CO$_2$Et) | 6,25 mmol according to Ex. 1 | Diethyl ether | −74° | EtO$_2$C-CH(NHTos)-CH$_2$CH=CH$_2$ [a] | 34 | b | 26 | G |
| 26 | 8 mmol (9-phenanthrenecarbaldehyde) | 10 mmol according to Ex. 1 | Diethyl ether | −74° | 9-phenanthrenyl-CH(OH)-CH$_2$CH=CH$_2$ [a] | 60 | b | 92 | H |
| 27 | 8 mmol (piperonal) | 10 mmol according to Ex. 1 | Diethyl ether | −74° | piperonyl-CH(OH)-CH$_2$CH=CH$_2$ [a] | 40 | b | ≧95 | H |

[a] absolute configuration unknown
[b] angle of rotation not determined
ToS = tosyl

EXAMPLES 28-30

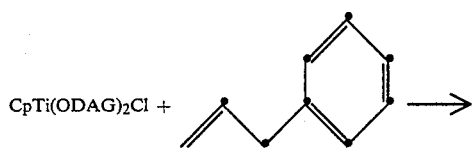

mixture is stirred for 2 hours. 30 ml of 45% aqueous NH4F solution are added to the solution, and the mixture is filtered and extracted with ether. The organic phase is washed twice with saturated NaCl solution, dried by means of MgSO4 and evaporated.

Chromatography over silica gel (3:1 hexane/ether) gives 1.02 g (3.7 mmol) of the alcohol III (56% yield); 86% ee, determined by method C. The reaction takes place with a 100% selectivity of conversion to anti.

TABLE 2

| Ex. | Carbonyl compound | Titanium complexes | Reaction conditions S | T[°C.] | Product | Yield [%] | % ee | Method | Diastereomer selectivity |
|---|---|---|---|---|---|---|---|---|---|
| 29 | 7 mmol, CH3-CO-H | 126 ml (8 mmol) of solution II from Ex. 28 | Diethyl ether, THF | −74° | (ketone product with CH3, phenyl, vinyl) | 70 | 86 | C | 100% anti |
| 30 | 7 mmol, PhCHO | 126 mmol (8 mmol) of solution II from Ex. 28 | Diethyl ether, THF | −74° | (alcohol product with OH, phenyl, vinyl) | 80 | 80 | C | 100% anti |

THF = Tetrahydrofuran

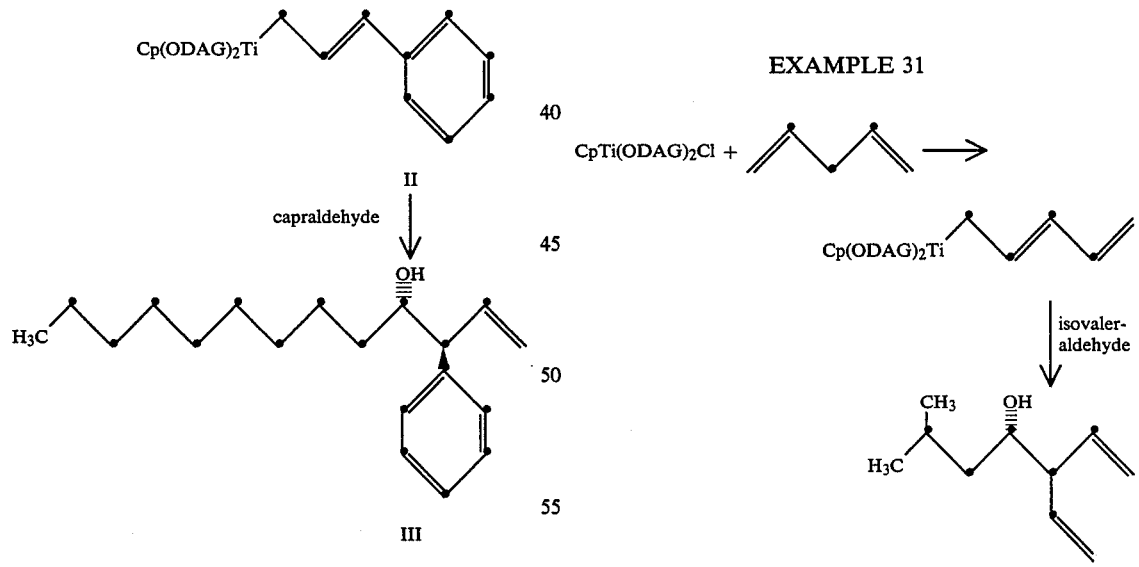

EXAMPLE 31

2.95 g (25 mmol) of allylbenzene in 170 ml of absolute tetrahydrofuran are reacted at −27° C. with 15.63 ml of n-butyllithium solution (1.6 M in hexane), and the mixture is then stirred for 60 minutes at RT (red coloration). This solution is added dropwise at 0° C. to 25 mmol of CpTi(ODAG)2Cl, dissolved in 270 ml of absolute ether, and the mixture is stirred for a further 30 minutes. The resulting solution of II is also used for Examples 29 and 30 (cf Table 2).

1.24 ml (6.6 mmol) of capraldehyde are added at −78° C. to 126 ml (8 mmol) of solution II, and the 1.23 ml (12 mmol) of 1,4-pentadiene in 20 ml of absolute tetrahydrofuran are reacted at −60° C. with 6.25 ml of n-butyllithium solution (1.6M in hexane), and the mixture is then stirred for 30 minutes at RT. This solution is added dropwise at 0° C. to 100 mmol of CpTi(O-DAG)2Cl, dissolved in 105 ml of diethyl ether, and the mixture is stirred for a further 30 minutes. 1.08 ml (10 mmol) of isovaleraldehyde are added at −78° C., and the mixture is stirred for 2 hours.

30 ml of 45% aqueous NH4F solution are added to the solution, and the mixture is filtered and extracted with ether. The organic phase is washed twice with saturated NaCl solution, dried by means of MgSO4 and evaporated.

The crude product is suspended in 100 ml of 0.2N HCl and stirred for 1.5 hours at room temperature. The aqueous phase is extracted 4 times with ether. The combined organic phases are washed twice with water and twice with saturated NaCl solution, dried by means of MgSO4 and evaporated.

Chromatography over silica gel (4:1 hexane/ether) gives 1.24 g (8 mmol) of the alcohol I (80% yield), 90% ee determined by method C.

EXAMPLE 32

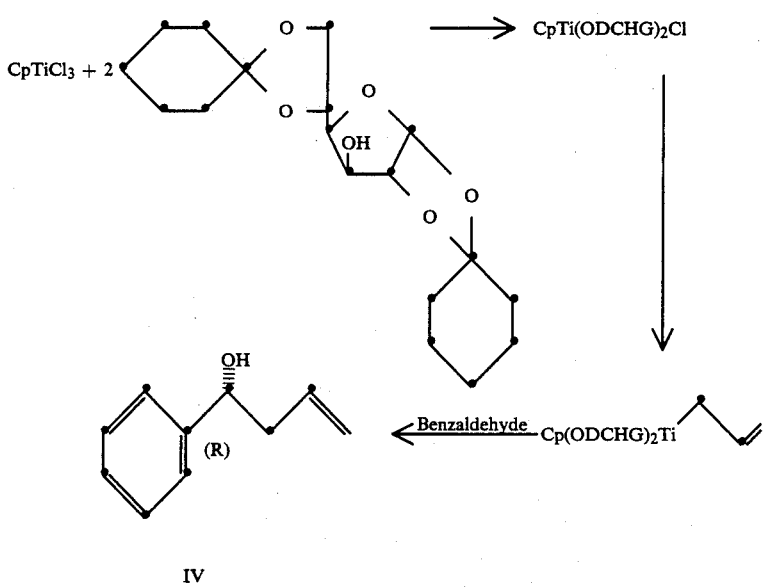

IV 2.15 g (9.8 mmol) of cyclopentadienyltitanium trichloride are dissolved in 60 ml of diethyl ether, and 6.33 g (19.6 mmol) of dicyclohexylideneglucose are added at RT. 2.8 ml (20 mmol) of triethylamine, dissolved in 25 ml of diethyl ether, are added dropwise in the course of 30 minutes. After 2 hours the triethylamine hydrochloride formed is filtered off under argon.

3.8 ml (9.8 mmol) of allylmagnesium chloride (2.6M solution in tetrahydrofuran) are added to the filtrate at 0° C., and the mixture is stirred for a further hour.

0.89 ml (8.8 mmol) of benzaldehyde is added at $-74°$ C. and the mixture is stirred for a further 2 hours. 30 ml of 45% aqueous NH4F solution are added to the solution, and the mixture is filtered and extracted with ether. The organic phase is washed twice with saturated NaCl solution, dried by means of MgSO4 and evaporated. Chromatography over silica gel (5:1 hexane/ether) gives 0.72 g (4.9 mmol) of the alcohol IV (56% yield); 75% ee determined by method A [[$\alpha$]$_D$=36.7° C., (c 6.22, benzene)].

EXAMPLE 33

The reaction with 1,2:4,5-di-O-isopropylidene-D-fructopyranose (HDIFP) instead of dicyclohexylideneglucose is carried out analogously to Example 32. 0.7 g (4.7 mmol) of the alcohol IV is obtained (75% yield); 52% ee, determined by method A [[]$\alpha_D$=25.1° C., (c 6.22, benzene)].

EXAMPLE 34

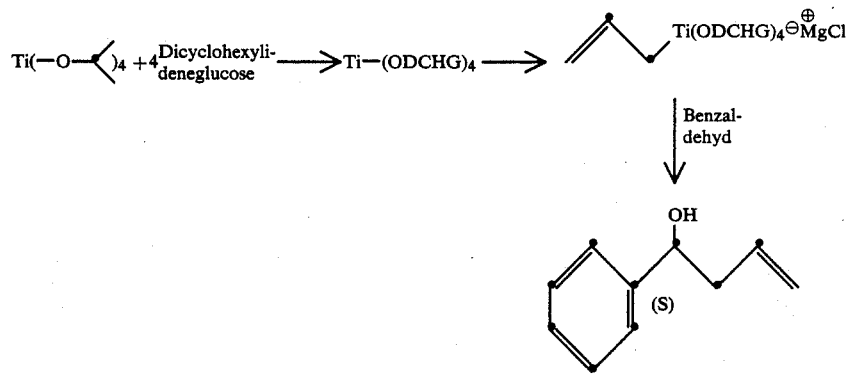

3.7 ml (12.5 mmol) of tetraisopropyl orthotitanate and 17.0 g (50 mmol) of dicyclohexylideneglucose are dissolved in 400 ml of cyclohexane. 250 ml (cyclohexane and 50 mmol of isopropanol) are then distilled off under normal pressure. The mixture is evaporated to dryness under a high vacuum, and the residue is dissolved in 100 ml of diethyl ether. 8 ml (10 mmol) of allylmagnesium chloride (1.25 molar in tetrahydrofuran) are added to the solution at 0° C., and the mixture is stirred for a further hour.

0.81 ml (8 mmol) of benzaldehyde are added at −74° C., and the mixture is stirred for a further 2 hours. 30 ml of 45% strength aqueous NH$_4$F solution are added to the solution, and the mixture is filtered and extracted with ether. The organic phase is washed twice with saturated NaCl solution, dried by means of MgSO$_4$ and evaporated.

Chromatography over silica gel (5:1 hexane/ether) gives 0.64 g (4.32 mmol) of (S)-1-phenyl-3-buten-1-ol (54% yield); 77% ee, determined by method C.

EXAMPLE 35

The reaction is carried out with diacetoneglucose instead of dicyclohexylideneglucose analogously to Example 34. 0.75 g (5.07 mmol) of (S)-1-phenyl-3-buten-1-ol are obtained (63% yield); 55% ee, determined by method C.

EXAMPLE 36

Ti(CH$_3$)$_4$ ⟶ CH$_3$Ti(ODAG)$_3$

↓ Benzaldehyde

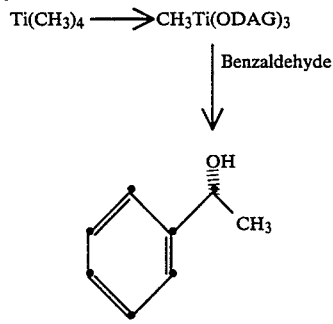

1.10 ml (10 mmol) of titanium tetrachloride are added at −74° C. to 60 ml of diethyl ether (yellow suspension). 25 ml (40 mmol) of methyllithium (1.6 molar in diethyl ether) are added dropwise in the course of 15 minutes; the green solution is stirred for a further 30 minutes at −74° C. 7.81 g (30 mmol) of diacetoneglucose in 150 ml of diethyl ether are added dropwise in the course of 70 minutes. After a further 10 minutes 0.90 ml (9 mmol) of benzaldehyde are added and the mixture is warmed up to RT overnight.

30 ml of 45% aqueous NH$_4$F solution are added to the solution, and the mixture is filtered and extracted with ether. The organic phase is washed twice with saturated NaCl solution, dried by means of MgSO$_4$ and evaporated. Chromatography over silica gel (1:5 hexane/ether) gives 0.8 g (6.55 mmol) of R-(+)-1-phenylethanol (82% yield); 62% ee, determined by method C.

EXAMPLE 37

(3R)-Hydroxycaprinic acid 70 mmol of lithium dicyclohexylamide in 150 ml of ether [14.50 g (80 mmol) of dicyclohexylamine; 43.7 ml (70 mmol) of 1.6M butyllithium in hexane] are initially taken, under argon at −73° C.

6.96 g (60.0 mmol) of tert.-butyl acetate are dissolved in 842 ml (80 mmol) of a 0.095M solution in toluene of ClTicp(ODAG)$_2$, and this solution is added dropwise to the lithium dicyclohexylamide solution in the course of 4 hours at −72° to −70° C.

The reaction solution was stirred for 1 hour at −73° C. and slowly (30 minutes) warmed up to −35° C. After being stirred for 30 minutes at −35° C., the solution is cooled to −74° C. and 7.69 g (60.0 mmol) of octanal (caprinaldehyde) in 35 ml of ether are added dropwise in the course of 45 minutes.

The reaction solution is stirred for 45 minutes at −74° C. and 150 ml of 45% aqueous NH$_4$F solution are added. The solution is filtered and extracted with ether. The organic phase is washed twice with saturated NaCl solution, dried by means of MgSO$_4$, filtered and evaporated.

The crude product (58.46 g of yellowish, oily crystals) is suspended in 1 l of 0.1N HCl and stirred at RT for 1.5 hours.

The aqueous phase is extracted 4 times with ether (150 ml). The combined organic phases are washed with twice 50 ml of water and twice 50 ml of saturated NaCl solution, dried by means of MgSO$_4$, filtered and evaporated.

The crude product (14.32 g of a yellow oil) is distilled (93° C./0.02 mbar) and affords 12.56 g (51.40 mmol; 85%) of the ester t.-butyl (3R)-hydroxycaprate in the form of a yellowish oil.

30 ml of trifluoroacetic acid are added at 0° C. to 5.11 g (20.91 mmol) of the ester, and the mixture is stirred for 1.5 hours at RT in vacuo (~50 mbar). The reaction solution is diluted with 50 ml of toluene and evaporated. The crude product is evaporated twice more, using 30 ml of toluene each time. 4.08 g of brown crystals are obtained, 95% ee (method C). Crystallization from 25 ml of cyclohexane gives 1.58 g (8.39 mmol: 40%) of colorless crystals and 2.15 g (11.42 mmol; 54%) of yellowish crystals were isolated from the mother liquor.

EXAMPLE 38

2′,6′-Dimethylphenyl (2R,3S)-2,4-dimethyl-3-hydroxypentanoate 1.42 ml (2.2 mmol) of a solution of n-butyllithium in hexane are added dropwise at −20° C. to a solution of 0.4 ml (2.4 mmol) of cyclohexylisopropylamine (freshly distilled over CaH$_2$) in 10 ml of ether. After 15 minutes, 357 mg (2 mmol) of 2,6-dimethylphenyl propionate, dissolved in 30 ml of a 0.085M solution of ClTiCp-(ODAG)$_2$ in ether, are added dropwise at −78° C. and in the course of 1.5 hours. After 2 hours at −78° C. and 30 minutes at −30° C., 0.18 ml (2 mmol) of 2-methylpropanal are added at −78° C. After 2 hours at −78° C., 40 ml of 45% aqueous NH$_4$F solution are added dropwise, the cooling bath is removed and 30 ml of 2N HCl are then added at RT. The clear aqueous phase is separated off in a separating funnel and extracted once with ether. The combined organic phases were washed with saturated NaCl solution, dried by means of MgSO$_4$ and evaporated.

70 ml of 0.1N HCl are added to the residue obtained, and the mixture is stirred vigorously for 1.5 hours and then extracted twice with ether. The organic phases are washed with saturated NaCl solution, dried by means of MgSO$_4$ and evaporated. Flash chromatography of the crude product over SiO$_2$ using 5:1 hexane/ethyl acetate gives 230 mg (46%) of 2,6-dimethylphenyl (2R,3S)-2,4-dimethyl-3-hydroxypentanoate, melting point 58.5°–59.5° C. $[\alpha]_D^{RT}$: +15.7° (c=1, CHCl$_3$) ee≧95% (method C). The carboxylic acid, prepared by basic hydrolysis, has an $[\alpha]_D^{RT}$ of +10.6° (c=0.16, CHCl$_3$).

EXAMPLE 39

2',6'-dimethylphenyl (+)-2-fluoro-2-phenyl-3-hydroxypentanoate 2.5 mmol of lithium diisopropylamide are prepared by means of a 1.6 molar solution of butyllithium in hexane and 0.255 g of diisopropylamine in 10 ml of THF under a protective gas and at −30° C. to room temperature. 2.0 mmol of racemic 2',6'-dimethylphenyl 2-fluoro-2-phenylacetate (prepared by DAST fluorination of racemic ethyl mandelate and transesterification with 2,6-dimethylphenol) in 1 ml of tetrahydrofuran are added dropwise slowly at −78° C., and 23 ml of a 0.1 molar solution in ether of CpTi(ODAG)$_2$Cl are then added under the same conditions. After stirring for 2 hours, 7 mmol of freshly distilled propionaldehyde in a little tetrahydrofuran are added dropwise at −78° C., and the reaction solution is warmed up to RT gradually. After being worked up by hydrolysis (4N HCl) and extraction with ether, the residue is purified by flash chromatography (9:1 hexane/ethyl acetate) over silica gel. After the combined product fractions have been evaporated, 0.250 g (40%) of a semi-crystalline 7:1 mixture of diastereomers of 2',6'-dimethylphenyl 2-fluoro-2-phenyl-3-hydroxypentanoate is isolated. The two diastereomers can be distinguished readily by means of the methyl group signals in the $^1$H-NMR spectrum.

The principal diastereomer shows the following resonance positions in the 300 MHz $^1$H-NMR spectrum (CDCl$_3$): 7.66 ppm (m, 2 aromatic H); 7.45 ppm (m, 3 aromatic H); 7.00 ppm (s, broad, 3 aromatic H); 4.41 ppm (m, 1H, C$\underline{H}$—OH); 1.88 (s, broad, 6H, aromatic C$\underline{H}_3$); 1.76 ppm (m, 2H, C$\underline{H}_2$); 1.13 ppm (t, j=7 Hz, 3H, C$\underline{H}_3$).

The subsidiary diastereomer differs significantly in the following resonance signals: 4.50 ppm (m, 1H, C$\underline{H}$—OH); 1.92 ppm (s, broad, 6H, aromatic C$\underline{H}_3$); 1.45 ppm (m, 2H, C$\underline{H}_2$); 1.02 ppm (t, j=7 Hz, 3H, C$\underline{H}_3$).

It was possible to determine the enantiomer excess for the two diastereomers by means of $^1$H-NMR shift experiments (method D). The ee values were determined on the basis of the δΔ values of the aliphatic CH$_3$ groups at 1.13 and 1.02 ppm:

ee value of the principal diastereomer: ≧90%
ee value of the subsidiary diastereomer: ≧50%
[α]$_D^{25}$ of the principal diastereomer = +12.03 (c=1.005, EtOH)

EXAMPLE 40

Ethyl α-amino-β-hydroxycaproate 2.5 ml of n-butyllithium (1.6 M in hexane, 4.08 mmol) are added at −40° to −35° C. and with the exclusion of air to a solution in 20 ml of tetrahydrofuran of 0.75 ml (4.49 mmol) of cyclohexylisopropylamine, freshly distilled over CaH$_2$, and the mixture is kept at this temperature for 20 minutes and is then cooled to −78° C. A solution of 1.0 g of the protected glycine ethyl ester* in 20 ml of tetrahydrofuran is added dropwise, the mixture is stirred for a further hour, the sugar/titanium complex (54 ml of ClCpTi(ODAG)$_2$, 0.09M in ether; 4.9 mmol) is added, the mixture is again stirred for an hour and 0.405 ml (4.49 mmol) of butyraldehyde in 15 ml of tetrahydrofuran is added to the brown reaction solution. The mixture is stirred for 22 hours at −78° C. and is then hydrolysed at −78° C. by adding 50 ml of a buffer solution (0.41N Na$_2$HPO$_4$; 0.28N KH$_2$PO$_4$) and is warmed up to RT. Partitioning the reaction mixture between 3 portions of ether, 2 portions of water and finally saturated NaCl solution gives a partly crystalline mixture of the reaction product and diacetoneglucose. The diacetoneglucose is separated quantitatively from the reaction product (in the hexane phase) by partitioning this mixture further between 3 portions of hexane and 4 portions of 4:1 CH$_3$CN/H$_2$O. 970 mg of an oil are obtained The crude product is dissolved in 25 ml of tetrahydrofuran, 5 ml of H$_2$O and 1 ml of acetic acid, and the mixture is stirred at RT for 3 hours. The hydrolysis mixture is evaporated and chromatographed (silica gel; 93:5:2 CH$_2$Cl$_2$/EtOH/Et$_3$N): 164.4 mg (23%) of pure threo product followed by 124.3 mg (17%) of a mixture of the threo and the erythro products.

Analytical data of the threo product: melting point 59-°61° C.; ee 95% (methods D and I), [α]$_D^{25}$ = −16.3° (c=0.959, ethanol).

1H-NMR: (CDCl$_3$) 0.95 (t, J=7, 3H, H$_3$C), 1.30 (t, J=7, 3H, H$_3$C), 1.3–1.6 (m, 4H, 2H$_2$C), 2.26 (sb, 3H, HO, H$_2$N), 3.36 (d, J=5, 1H, HC$_\alpha$), 3.74–3.82 (m, 1H, HC$_\beta$), 4.22 (q, J=7, 2H, H$_2$C).

Analytical data of the erythro product:
1H-NMR: (CDCl$_3$) 0.93 (t, J=7, 3H, H$_3$C), 1.30 (t, J=7, 3H, H$_3$C), 1.3–1.6 (m, 4H, 2H$_2$C), 2.90 (sb, 3H, HO, H$_2$N), 3.64 (d, J=4, 1H, HC$_\alpha$), 3.89–3.91 (m, 1H, HC$_\beta$), 4.15–4.30 (m, 2H, H$_2$C).

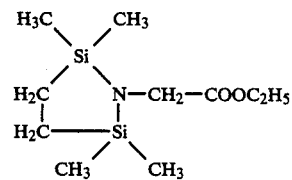

The threo/erythro allocation is made at the free acid stage, based on the chemical shifts of H$_\alpha$ in the $^1$H-NMR spectrum [*Literature*, Y. Ariyoshi and N. Sato, Bull. Chem. Soc. Japan 44, 3435 (1971)].

EXAMPLE 41

Preparation of (S)-(−)-ipsenol (a) 88 g (0.4 mol) of cyclopentadienyltitanium trichloride are initially placed in 3 l of absolute toluene under argon, and 208.2 g (0.8 mol) of freshly sublimed diacetoneglucose are then added. 83.0 g (0.82 mol) of triethylamine, dissolved in 500 ml of absolute toluene, are added dropwise to this mixture at room temperature in the course of 1 hour. After vigorous stirring for 5 hours, the precipitated amine hydrochloride is filtered off under argon through Celite and the precipitate is washed with a little absolute toluene. This gave a solution of 4,186 ml of the sugar complex according to Example 1a, which is employed without further treatment for the following reaction stage.

(b) Preparation of

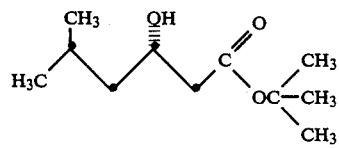

69 g (0.38 mol) of dicyclohexylamine are dissolved in 1 l of diethyl ether and cooled to −30° C.; 225 ml of a 1.6 molar solution of n-butyllithium in hexane are added at this temperature in the course of 40 minutes. After being stirred at −25° C. for 30 minutes the mixture is cooled to −78° C. 3,977 ml of the toluene solution (a), mixed with 40.7 g (0.35 mol) of t.-butyl acetate, are added dropwise to the mixture at −70° to −78° C. in the course of 3 hours. The reaction mixture is then warmed up to −30° C. in the course of 1 hour, kept at this temperature for 30 minutes and then again cooled to −78° C. 30.3 g (0.35 mol) of isovaleraldehyde, dissolved in 100 ml of diethyl ether, are added dropwise at this temperature in the course of 45 minutes; the reaction solution is then stirred for a further 90 minutes at −78° C., and 1 l of a 45% aqueous ammonium fluoride solution is then added. The precipitate formed is filtered off and washed with twice 100 ml of toluene. The aqueous phase is separated off from the organic phase and extracted with twice 250 ml of ether. The combined organic phases are then washed with 3 times 100 ml of water, dried by means of magnesium sulfate and evaporated on a rotary evaporator. 4.5 l of 0.1N hydrochloric acid is added to the residue (307 g), and the mixture is stirred vigorously for 2 hours. The resulting mixture is extracted in a separating funnel with 3 times 600 ml of ether. The combined ether phases are separated over Celite from a small amount of precipitate and are then dried by means of magnesium sulfate. The solvent is removed in vacuo and the residue is distilled; this gives 37.1 g of the desired t.-butyl 3-hydroxy ester in the form of a colourless liquid having a boiling point of 53°-54° C. (0.39 mbar) (53% of theory); $[\alpha]_D^{25}$ +14.39° (c=1.529 in CHCl$_3$), 96% ee (methods A and B).

(c) Preparation of

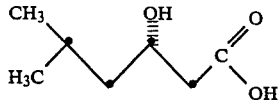

200 ml of trifluoroacetic acid are added at 0° C. to 37.1 g (0.183 mol) of t.-butyl β-hydroxy ester according to (b). The mixture is stirred for 1 hour at room temperature under reduced pressure (65–130 mbar). The trifluoroacetic acid is then removed in vacuo and the crude β-hydroxy-acid obtained is purified. The residue is dissolved in 150 ml of 2N sodium hydroxide solution and extracted with 150 ml of ether. The basic phase is acidified carefully with 10N hydrochloric acid to pH 3 and extracted with 4 times 400 ml of methylene chloride. The organic phase is dried by means of magnesium sulfate, and the solvent is removed in vacuo. This gives 22.8 g (0.156 mol) of the desired hydroxy-acid (85% of theory). Recrystallization from 1.25 l of cyclohexane gives 19.35 g (0.132 mol) of the pure enantiomer (+)-R-2-hydroxy-acid (according to method C) of melting point 82°–83° C. (38% of theory, relative to the amount of isovaleraldehyde employed), $[\alpha]_D^{25}$=+15.5° (c=1.023 in CHCl$_3$).

(d) Preparation of

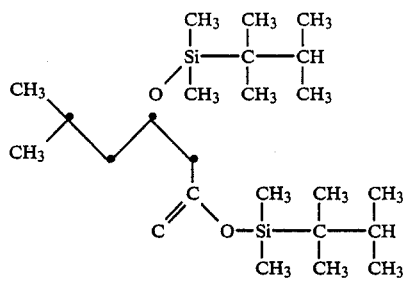

9.4 g (0.064 mol) of the β-hydroxy-acid (c) are dissolved in 35 ml of dimethylformamide, and 12.71 g (0.187 mol) of imidazole and 26.47 g (0.148 mol) of dimethyl-(2,3-dimethyl-2-butyl)-chlorosilane (thexyldimethylchlorosilane) are added. After being stirred for 24 hours, the reaction mixture is poured into 200 ml of water and extracted with 200 ml of hexane. The aqueous phase is extracted additionally with twice 50 ml of hexane. The combined organic phases are dried by means of magnesium sulfate and are then evaporated in vacuo. The residue obtained is filtered off. 26.97 g (0.063 mol) of product were obtained in the form of a colourless liquid of boiling point 119°–120° C. (0.0325 mbar) (98% of theory). $[\alpha]_D^{25}$=9.19° (c=1.07 in toluene).

(e) Preparation of

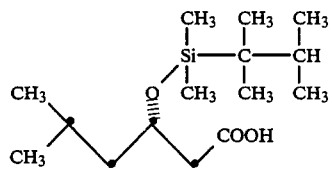

21.5 g (0.05 mol) of bis-silylated hydroxy-acid (d) are dissolved in 200 ml of tetrahydrofuran, and 100 ml of water and 100 ml of 1 N NaHCO$_3$ solution are added. The two-phase system is stirred vigorously for 24 hours, 500 ml of water are then added and the mixture is acidified carefully with 75 ml of 2N hydrochloric acid. 300 ml of ether are added in order to improve the separation of the phases. The organic phase is separated off in a separating funnel, dried by means of magnesium sulfate and evaporated in vacuo. This gives a mixture of silanol and the desired thexyldimethyl-silyl-protected β-hydroxy-acid. Thexyldimethylsilanol is removed virtually completely by distillation by warming the mixture to 50° C. under reduced pressure (0.1 mm Hg). 2Thexyldimethylsilyloxy-4-methylcaproic acid is isolated in a pure state by chromatography over silica gel using 4:1 hexane/ethyl acetate: 12.96 g (90% of theory) of a colourless liquid.

1H-NMR: (60 MHz, CDCl$_3$); 0.18 (s, 6H), 0.82 (d, 6H), 0.88 (d, 12H), 1.2–1.5 (m, 3H), 1.6 (m, 1H), 2.4 (dd, 2H) 4.1 (m, 1H). $[\alpha]_D^{25}$=−2.62° (c=0.994 in chloroform).

(f) Preparation of

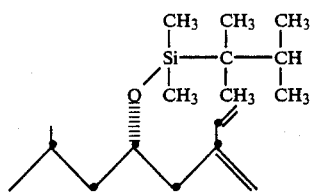

16.82 g (0.0584 mol) of the acid (e) are dissolved in 50 ml of methylene chloride, and 9.08 ml (0.0642 mol) of 1-chloro-1-dimethylamino-2-methylprop-1-ene are added, with stirring, at 0° C. The reaction mixture is warmed slowly to room temperature. After stirring for a further 30 minutes, the solvent is removed in vacuo, the residue is taken up in 100 ml of ether, and 11.68 g (0.0613 mol) of Cu(I)I are added at −30° C. The resulting white suspension is cooled further to −78° C., and is reacted with 64.4 ml (0.082 mol) of a 1.25M ethereal solution of trimethylsilylmethylmagnesium chloride. The reaction mixture is warmed slowly to 0° C. and is stirred for a further hour at this temperature. 11.56 ml of a 5.05M solution of ammonium chloride are then added dropwise carefully, and the whole mixture is filtered through Hyflo. The clear filtrate is dried by means of magnesium sulfate, and 50 ml of benzene are added. The solvent is then removed in vacuo and the residue is employed without further purification for the subsequent reaction.

10.47 g of the residue are dissolved in 50 ml of tetrahydrofuran, and 64.7 ml of a 1M solution of vinylmagnesium bromide are added dropwise at 0° C. The reaction mixture is then stirred for 18 hours at room temperature. The excess Grignard reagent is then destroyed by adding a mixture of 150 ml of saturated ammonium chloride solution and 25 ml of 2N hydrochloric acid. Extraction with 3 times 50 ml of ether, drying the organic phases by means of magnesium sulfate and removing the solvent in vacuo gives 9.8 g of a slightly yellow liquid which is employed without further treatment in the subsequent reaction stage.

50 ml of acetic acid saturated with sodium acetate are added to the residue (9.8 g), and the mixture is stirred for 5 hours at 50° C. The reaction mixture is then poured into 400 ml of ice/water and extracted with 3 times 100 ml of hexane. The combined organic phases are washed with twice 30 ml of saturated NaHCO$_3$ solution and are dried by means of magnesium sulfate. After the solvent has been removed in vacuo, the residue (18.7 g) is purified by chromatography over 150 g of silica gel (eluant hexane). 7.41 g of a product are isolated in the form of a colourless liquid (43% of theory, relative to the amount of thexyldimethylsilyloxy-4methylcaproic acid employed). Boiling point 88°–90° C. (0.13 mbar); $[\alpha]_D^{25} -11.5°$ (c=1.01 in ethanol). (g)

Preparation of (−)-(S')-ipsenol

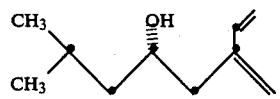

23.7 g (0.075 mol) of tetrabutylammonium fluoride trihydrate are added to 7.41 g (0.025 mol) of thexyl-dimethyl-silyl-protected (−)-S-ipsenol according to (f) in 100 ml of tetrahydrofuran, and the mixture is stirred for 40 hours at room temperature. 200 ml of water are then added to the reaction mixture, which is extracted with 3 times 100 ml of ether. The combined ether phases are washed with 20 ml of saturated sodium chloride solution and are then dried by means of magnesium sulfate. The solvent is then removed in vacuo and the residue is distilled. This gives 4.1 g of a colourless liquid of boiling point 76°–85° C. (6.5 mbar), which contains approx. 15–20% of thexyldimethylsilanol as an impurity. After chromatographing the mixture over 200 g of Alox using methylene chloride as solvent, 3.48 g of pure (−)-S-ipsenol (90% of theory) are isolated, boiling point 78°–79° C. (6.5 mbar). $[\alpha]_D^{25} -17.62°$ (c=1.028 in ethanol).

What is claimed is:

1. A compound of the formulae I and Ia

and

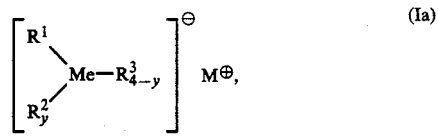

in which Me is tetravalent titanium, zirconium or hafnium,

R$^1$ is linear or branched alkyl, alkenyl, alkynyl, cycloalkyl or cycloalkenyl which is unsubstituted or substituted by C$_1$–C$_4$-alkyl, or is aryl, alkaryl, aralkyl, alkaralkyl, aralkenyl, alkaralkenyl, aralkynyl or alkaralkynyl which are unsubstituted or monosubstituted or polysubstituted by (C$_6$H$_5$)P—, (R$^5$O)P(O)—, R$_3^5$Si—, R$_3^5$SiO—, R$^5$SO$_2$—, —S—C$_2$–C$_4$-alkylene-S—, —O—C$_2$–C$_4$-alkylene-O—, R$^5$ being phenyl, benzyl or C$_1$–C$_8$-alkyl, or is cyano, F, nitro, C$_1$–C$_{12}$-alkylthio, C$_1$–C$_{12}$-alkoxy, secondary amino or -COR$^4$ in which R$^4$ is the radical of a monohydric alcohol; or R$^1$ is a radical of an enol, enamine or enehydrazine;

R$^2$ is cyclopentadienyl, alkoxy, cycloalkoxy, cycloalkylalkoxy, aryloxy, aralkyloxy, alkylthio, arylthio or aralkylthio which is unsubstituted or substituted by alkyl, alkenyl, alkoxy, cycloalkyl, aryl, aralkyl, trialkoxysilyl, trialkylsilyl or halogen; or R$^2$ is halogen, pseudohalogen, acyloxy, acylamino or trialkylsilyloxy, R$^3$ is the radical, diminished by a hydroxyl or thiol group or an amine hydrogen atom, of a protected, monohydroxy-functional, monothiol-functional or monoamine-functional, optically active sugar, thiosugar or amino-sugar or derivatives thereof belonging to the group of sugar alcohols; esters of a sugar acid, aldo-sugar acid or keto-sugar acid; aminosugars, sugar mercaptals or deoxy-sugars, x is 0, 1 or 2 and y is 0, 1, 2 or 3 and M⊕ is Li⊕, Na⊕, K⊕, MgY⊕, ZnY⊕, CdY⊕, HgY ⊕, CuY ⊕ or quaternary ammonium, Y being halogen.

2. A compound according to claim 1, in which R$^1$ is linear or branched C$_1$–C$_{18}$-alkyl, C$_2$–C$_{12}$-alkenyl, C$_2$–C$_{12}$-alkynyl, cycloalkyl having 3–8 ring C atoms, cycloalkenyl having 3 to 8 ring C atoms, C$_6$–C$_{12}$-aryl, C$_7$–C$_{16}$-alkaryl or aralkyl, C$_8$–C$_{16}$-alkaralkyl, C$_8$–C$_{16}$- aralkenyl, $C_9-C_{16}$-alkaralkenyl, $C_8-C_{16}$-aralkynyl or $C_9-C_{16}$-alkaralkynyl which is unsubstituted or monosubstituted or polysubstituted by secondary amino, cyano, nitro, $C_1-C_6$-alkylthio, $C_1-C_6$-alkoxy or $-COR^4$ in which $R^4$ is $C_1-C_{12}$-alkoxy; or $R^1$ is a radical of an enol, enamine or enehydrazine which is attached via the enol oxygen atom or via the enamine nitrogen atom.

3. A compound according to claim 2, in which $R^1$ is linear of branched $C_1-C_6$-alkyl, $C_2-C_6$-alkenyl, $C_2-C_6$-alkynyl, cycloalkyl having 3–6 ring C atoms, cycloalkenyl having 3 to 6 ring C atoms, phenyl, $(C_1-C_{10}$-alkyl)-phenyl, phenyl-$(C_1-C_2$alkyl), $(C_1-C_8$-alkyl)-phenyl-$(C_1-C_2$-alkyl), phenylvinyl, phenylethynyl, phenylpropargyl, $(C_1-C_8$-alkyl)-phenylvinyl, $(C_1-C_8$-alkyl)-phenylethynyl or $(C_1-C_7$-alkyl)-phenylpropargyl which is unsubstituted or monosubstituted or polysubstituted by secondary amino, cyano, nitro, $C_1-C_6$-alkoxy, $C_1-C_6$-alkylthio or $-COR^4$ in which $R^4$ is $C_1-C_{12}$-alkoxy; or $R^1$ is the radical of an enol, enamine or enehydrazine having up to 20 C atoms which is attached via an enol oxygen atom or enamine nitrogen atom.

4. A compound according to claim 2, in which $R^1$ is linear or branched $C_1-C_4$-alkyl, vinyl, allyl, ethynyl, propargyl, cyclopentyl, cyclohexyl, cyclopentenyl, cyclohexenyl, phenyl, methylphenyl, benzyl, 1-phenyleth-2-yl, methylbenzyl, phenylvinyl, methylphenylvinyl, phenylethynyl, phenyl propargyl, methylphenylethynyl, dimethylphenylethynyl or dimethylphenylpropargyl which is unsubstituted or monosubstituted or polysubstituted by secondary amino, cyano, nitro, $C_1-C_6$-alkoxy, $C_1-C_6$-alkylthio or $-COR^4$ in which $R^4$ is $C_1-C_{12}$-alkoxy; or $R^1$ is the radical of an enol, enamine or enehydrazine having 2–16 C atoms which is attached via the enol oxygen atom or via the enamine nitrogen atom.

5. A compound according to claim 1, in which $R^2$ is cyclopentadienyl, $C_1-C_{18}$-alkoxy, $C_6-C_{12}$-aryloxy, $C_7-C_{16}$-aralkoxy, $C_1-C_{18}$-alkylthio, $C_6-C_{12}$-arylthio or $C_7-C_{16}$-aralkylthio which is unsubstituted or substituted by $C_1-C_6$-alkyl, $C_2-C_6$alkenyl, $C_1-C_6$-alkoxy, cycloalkyl having 5 or 6 ring C atoms, phenyl, benzyl, trialkoxysilyl having 1 to 6 C atoms in the alkoxy groups, trialkylsilyl having 1 to 6 C atoms in the alkyl groups, F, Cl or Br; or $R^2$ is halogen, pseudohalogen, $C_1-C_{18}$-acyloxy, $C_1-C_{18}$-acylamino or trialkylsilyloxy having 1 to 6 C atoms in the alkyl groups. $C_2-C_6$-alkenyl, $C_1-C_6$-alkoxy, cycloalkyl having 5 or 6 ring C atoms, phenyl, benzyl, trialkoxysilyl having 1 to 6 C atoms in the alk- oxy groups, trialkylsilyl having 1 to 6 C atoms in the alkyl groups, F, Cl or Br; or $R^2$ is halogen, pseudohalogen, $C_1-C_{18}$-acyloxy, $C_1C_{18}$-acylamino or trialkylsilyloxy having 1 to 6 C atoms in the alkyl groups.

6. A compound according to claim 5, in which $R^2$ is cyclopentadienyl, $C_1-C_6$-alkoxy, phenoxy, benzyloxy, $C_1-C_6$-alkylthio, phenylthio or benzylthio which is unsubstituted or substituted as stated in claim 5; or is Cl, Br, I, CN, CNS, CNO, $C_1-C_{12}$-acyloxy, $C_1-C_{12}$-acylamino or trialkylsilyloxy having 1 to 4 C atoms in the alkyl groups.

7. A compound according to claim 1, in which $R^3$ is the radical of a protected, monohydroxyfunctional, monothiolfunctional or monoaminofunctional $C_3-C_7$-monosaccharide or corresponding disaccharides or trisaccharides or derivatives thereof belonging to the group of the sugar alcohols; esters of a sugar acid, aldo sugar acid or keto sugar acid; or amino-sugars, deoxysugars or sugar mercaptals.

8. A compound according to claim 7, in which $R^3$ is the radical of a $C_5$ or $C_6$ monosaccharide or derivatives thereof.

9. A compound according to claim 7, in which $R^3$ is the radical of a protected furanose or pyranose.

10. A compound according to claim 1, in which the hydroxyl groups of the sugars and their derivatives are protected by $C_1-C_8$-acyl, $C_1-C_8$-alkyl, benzyl, diphenylmethyl, trityl, $C_1-C_8$-alkylidene, triphenylsilyl or trialkylsilyl having 1 to 8 C atoms in the alkyl groups, $(C_6H_5)_2Si=$, $(C_1-C_8$-alkyl$)_2Si$, $(C_6H_5)_2Sn=$ or $(C_1-C_8$-alkyl$)_{12}Sn=$.

11. A compound according to claim 1, in which $R^3$ is the radical of 1,2:5,6-di-O-isoppropylidene-α-glucofuranose which has been diminished by the hydroxyl hydrogen atom.

12. A compound according to claim 1, in which x is 1 and y is 1.

13. A compound according to claim 1, in which Y is Cl, Br or I.

14. A compound according to claim 1, in which $M\oplus$ is $Li\oplus$, $MgCl\oplus$, $MgBr\oplus$, $ZnCl\oplus$, $ZnBr\oplus$, CdCl, $CdBr\oplus$ or tetraalkylammonium having 1 to 6 C atoms in the alkyl groups.

15. A compound according to claim 1, in which Me is Ti, $R^1$ is allyl or 1-(t.-butoxy)-vinyl-1-oxy, $R^2$ is cyclopentadienyl and $R^3$ is the radical of 1,2:5,6-di-O-isprylidene-α-glucofuranose which has been diminished by the hydroxyl hydrogen atom.

* * * * *